United States Patent [19]

Burk et al.

[11] 4,163,797

[45] Aug. 7, 1979

[54] STABILIZED AQUEOUS AMIDE ANTIMICROBIAL COMPOSITION

[75] Inventors: George A. Burk, Bay City; Charles E. Reineke, Midland, both of Mich.

[73] Assignee: The Dow Chemical Company, Midland, Mich.

[21] Appl. No.: 860,541

[22] Filed: Dec. 14, 1977

[51] Int. Cl.$^2$ ............................................... A01N 9/20
[52] U.S. Cl. .................................... 424/304; 424/244; 424/273 R; 424/274; 424/320; 424/321; 424/322
[58] Field of Search ............... 424/304, 274, 320, 322, 424/244, 273, 321; 210/62

[56] References Cited

U.S. PATENT DOCUMENTS

| | | | |
|---|---|---|---|
| 3,078,277 | 2/1963 | Geering | 424/174 |
| 3,689,660 | 9/1972 | Burk et al. | 424/304 |
| 3,751,444 | 8/1973 | Solem et al. | 260/465.4 |
| 4,022,605 | 5/1977 | Konya et al. | 424/304 |

*Primary Examiner*—V. D. Turner
*Attorney, Agent, or Firm*—James B. Guffey

[57] ABSTRACT

Aqueous antimicrobial compositions which comprise a halogenated amide antimicrobial, such as 2,2-dibromonitrilopropionamide, a water miscible organic solvent such as a straight chain polyalkylene glycol (e.g., polyethylene glycol 200) or an ether thereof (e.g., a mono- or di-lower alkyl and/or phenyl ether) and water are stabilized against decomposition of the halogenated amide antimicrobial by the addition of a carbamoyl or sulfamoyl stabilizer, such as dimethyl formamide, sulfamide, urea, oxamide, biuret, caprolactam, succinimide, etc. The compositions, so stabilized, exhibit reduced rates of decomposition of the halogenated amide antimicrobial relative to the corresponding non-stabilized aqueous compositions.

20 Claims, No Drawings

STABILIZED AQUEOUS AMIDE ANTIMICROBIAL COMPOSITION

BACKGROUND OF THE INVENTION

This invention relates to stabilized aqueous antimicrobial compositions which comprise a halogenated amide as the active (i.e., antimicrobial) ingredient and to processes for their preparation.

Halogenated amides such as 2,2-dibromonitrilopropionamide are useful as antimicrobials in various applications. See, for example, Nolan et al., U.S. Pat. No. 2,419,888; Schmidt et al., U.S. Pat. No. 3,493,658; and CIBA S.A. Belgian Pat. No. 668,336. Certain halogenated amides are useful in the finishing of textiles, as taught by Chance et al., U.S. Pat. Nos. 3,350,164 and 3,403,174. Others are useful as slimicides in aqueous systems such as paper pulp and cooling towers and as sterilizing agents for drycleaning fluids. See, for example, Wolf, U.S. Pat. No. 3,647,610; Wolf, U.S. Pat. No. 3,649,166; Wolf et al., "2,2-Dibromo-3-Nitrilopropionamide, A Compound with Slimicidal Activity", *Applied Microbiology*, Vol. 24, No. 4, pp. 581-584 (1972); and Moyle et al., U.S. Pat. No. 3,928,575.

In the storage, shipment and use of such antimicrobial agents, it is often desirable to employ the antimicrobial agent in the form of a liquid concentrate composition wherein the halogenated amide antimicrobial is dissolved in a mixture of an organic solvent and water. However, the presence of water in such compositions often accelerate decomposition of the halogenated amide antimicrobial. See, for example, U.S. Pat. No. 3,689,660 and "Rates and Products of Decomposition of 2,2-Dibromo-3-Nitrilopropionamide", Exner et al., *J. Agr. Food Chem.*, Vol. 21, No. 5, pp. 838-842 (1973). Accordingly, in order to obtain adequate stability for many purposes, it has heretofore been necessary to resort to essentially anhydrous liquid concentrate compositions and it has therefore been necessary to essentially exclude water from the ingredients used in the preparation thereof.

Consequently, it is desirable to provide a means of reducing the adverse impact of water upon the aforementioned liquid concentrate compositions and to thereby provide (a) aqueous halogenated amide antimicrobial compositions having improved stability and (b) simplified, economical processes for the preparation of stable liquid concentrate compositions.

SUMMARY OF THE INVENTION

It has now been found that the rate of decomposition of the halogenated amide antimicrobial in the aforementioned aqueous liquid concentrate compositions is substantially reduced by the addition of a carbamoyl stabilizer, a sulfamoyl stabilizer or a combination thereof. Thus, in one aspect the instant invention is a stabilized aqueous antimicrobial composition which comprises (1) a water miscible organic solvent; (2) water; (3) a halogenated amide antimicrobial; and (4) a stabilizing amount of a carbamoyl stabilizer, which is different from the halogenated amide antimicrobial, a sulfamoyl stabilizer or a combination thereof. Typically, such composition has a pH of from about 2 to about 5 (preferably from about 3 to about 4).

In another aspect the instant invention is a process for preparing an aqueous halogenated amide antimicrobial composition wherein the aqueous component of such composition comprises the aqueous reaction medium in which the halogenated amide antimicrobial was prepared. Such process comprises the steps of:

(a) preparing the halogenated amide antimicrobial by the acid catalyzed reaction of a non-halogenated amide with halogen in aqueous solution;

(b) dissolving the resulting aqueous reaction mixture in a water miscible organic solvent; and (c) adding to the reaction mixture, or to the water miscible organic solvent solution thereof, a stabilizing amount of a carbamoyl stabilizer which is different from the halogenated amide antimicrobial, a sulfamoyl stabilizer or a combination thereof.

Typically, the aforementioned process also involves a pH adjustment step such that the composition resulting from such process has a pH of from about 2 to about 5, preferably from about 3 to about 4.

As used herein, the term "water miscible" means that the organic solvent is soluble in water (i.e., mixes or blends uniformly with water) at least to the degree required to achieve the desired solvent to water ratio in the aqueous composition and preferably such solvent is soluble in water in all proportions.

The terms "antimicrobial compound" and "halogenated amide antimicrobial" are used interchangeably herein and refer to halogenated amides which function as biocides (i.e., compounds which inhibit the growth of, or kills, microorganisms such as bacteria, molds, slimes, fungi, etc.).

As used herein, the term "carbamoyl stabilizer" refers to a saturated aliphatic or a saturated alicyclic compound containing a moiety of the formula —N($R_3$)C(O)— wherein $R_3$ is hydrogen or lower alkyl and wherein "saturated" refers to freedom from carbon to carbon unsaturation. The term "sulfamoyl stabilizer" refers to a saturated aliphatic or saturated alicyclic compound containing a moiety of the formula —N($R_3$)S(O)$_2$— wherein $R_3$ is hydrogen or lower alkyl and wherein "saturated" has the aforesaid meaning.

As used herein, the term "lower alkyl" refers to alkyl groups containing from 1 to about 6 carbon atoms such as methyl, ethyl, n-propyl, isopropyl, n-butyl-sec-butyl, t-butyl, n-pentyl and the like.

The term "stabilizing amount" as employed herein refers to an amount of stabilizer sufficient to measurably reduce the decomposition rate of the halogenated amide antimicrobial in the aqueous antimicrobial composition. The aforementioned reduction in the decomposition rate of the halogenated amide antimicrobial is, of course, relative to the decomposition rate encountered with a corresponding aqueous antimicrobial composition in the absence of the stabilizer under the same test conditions. Such reduction is deemed to be "measurable" if it is detectible (and reproducible) by the iodometric test method which is described hereinafter in conjunction with the working examples.

The aqueous antimicrobial compositions of the invention are useful as slimicides in aqueous systems such as paper pulping processes and cooling towers and as sterilizing agents for drycleaning fluids. Such compositions exhibit improved stability toward decomposition of the halogenated amide antimicrobial for extended periods under a wide variety of storage, packaging and handling conditions. They are easily handled and can be employed in the above applications pursuant to conventional techniques such as those described in U.S. Pat. No. 3,689,660.

The indicated process for preparing the aqueous antimicrobial composition is advantageous in that suitably stable compositions can be prepared without separation of the halogenated amide antimicrobial from the aqueous medium in which it was prepared.

DETAILED DESCRIPTION OF THE INVENTION

Halogenated amide antimicrobials employed in the practice of this invention are alpha-haloamides; that is, compounds which contain an amide functionality (i.e., a moiety of the formula

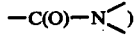

and which have at least one halogen atom on a carbon atom located adjacent to (i.e., in the alpha position relative to) the carbonyl group (i.e., the —C(O)— group) of such amide functionality. Advantageously, such halogenated amide antimicrobials are halogenated nitrilopropionamides or halogenated malonic diamides having the formula:

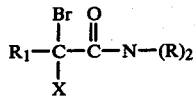

wherein:
X is hydrogen, halogen or a cyano radical, i.e., —C≡N, (preferably hydrogen, chlorine or bromine);
each R group is independently hydrogen, a monovalent "saturated hydrocarbon radical" or an inertly substituted monovalent "saturated hydrocarbon radical" or the two R groups are, jointly, a divalent "saturated hydrocarbon radical", or an inertly substituted divalent "saturated hydrocarbon radical", which, taken with the adjacent nitrogen atom, forms a heterocyclic ring having from 4 to about 10 ring members; and
$R_1$ is a cyano radical (i.e., —C≡N) or an amido radical having the formula:

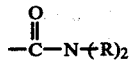

wherein R is as hereinbefore defined. (Preferably $R_1$ is a cyano radical.)

As used herein, the term "saturated hydrocarbon radical" refers to a hydrocarbon radical which is free from aliphatic carbon to carbon unsaturation. Thus, such term includes radicals such as alkyl, cycloalkyl, aryl, alkylaryl, arylalkyl, cycloalkylaryl, etc., and excludes radicals such as alkenyl, cycloalkenyl, alkynyl and the like.

As used herein, the term "inertly substituted saturated hydrocarbon radical" refers to a "saturated hydrocarbon radical" having one or more chain linkage or substituent which is "inert" in the sense that such chain linkage or substituent does not readily react with the ingredients of the aqueous antimicrobial composition. Suitable inertly substituted saturated hydrocarbon radicals thus include, for example, haloalkyl, haloaryl, halocycloalkyl, aminoalkyl, aminoaryl, aminocycloalkyl, hydroxyalkyl, hydroxyaryl, hydroxycycloalkyl, cyanoalkyl, cyanoaryl, cyanocycloalkyl, and the like.

The aforementioned halogenated amide antimicrobials of the formula I thus include brominated nitrilopropionamides (i.e., compounds of the formula I wherein $R_1$ is a cyano radical), such as 2-bromo-3-nitrilopropionamide, 2-bromo-2,3-dinitrilopropionamide, 2,2-dibromo-3-nitrilopropionamide, N-(n-butyl)-2-bromo-3-nitrilopropionamide; N,N-dimethyl-2,2-dibromo-3-nitrilopropionamide, 2-chloro-2-bromo-3-nitrilopropionamide, N-(n-propyl)-2-iodo-2-bromo-3-nitrilopropionamide, N-methyl-N-ethyl-2-fluoro-2-bromo-3-nitrilopropionamide, N-phenyl-2-cyano-2-bromo-3-nitrilopropionamide, N-cyclohexyl-2,2-dibromo-3-nitrilopropionamide, N-benzyl-2-bromo-3-nitrilopropionamide, N-(2,2-dibromo-3-nitrilopropionoyl)-piperidine and the like.

The aforementioned halogenated amide antimicrobials of the formula I also include mono- and di-bromomalonic diamides (i.e., compounds of the formula I wherein $R_1$ is an amido radical as hereinbefore described), such as 2-bromomalonic diamide, 2,2-dibromomalonic diamide, N-methyl-N'-ethyl-2-chloro-2-bromomalonic diamide, N-phenyl-2-iodo-2-bromomalonic diamide, and the like.

Among the aforementioned halogenated amide antimicrobials, those wherein, in the formula I, $R_1$ is a cyano radical, X is hydrogen, chlorine or bromine and each R is independently hydrogen, lower alkyl (e.g., an alkyl group of from 1 to about 6 carbon atoms) or phenyl are preferred, especially those of the formula I wherein each R independently is hydrogen or methyl and X is hydrogen or bromine. Such halogenated amide antimicrobials include 2-bromo-3-nitrilopropionamide, 2,2-dibromo-3-nitrilopropionamide, N-methyl-2-bromo-3-nitrilopropionamide, N-phenyl-2-bromo-2-chloro-3-nitrilopropionamide, N-methyl-2,2-dibromo-3-nitrilo-propionamide, N,N-dimethyl-2-bromo-3-nitrilopropionamide, N,N-diethyl-2,2-dibromo-3-nitrilopropionamide, and N,N-dimethyl-2,2-dibromo-3-nitrilopropionamide.

Also of particular interest are the dibrominated nitrilopropionamides (i.e., the halogenated amide antimicrobials of the formula I wherein X is bromine and $R_1$ is cyano) wherein each R independently is hydrogen, lower alkyl or phenyl. Such compounds include 2,2-dibromo-3-nitrilopropionamide, N-(n-butyl)-2,2-dibromo-3-nitrilopropionamide, N,N-dimethyl-2,2-dibromo-3-nitrilopropionamide, N-phenyl-N-methyl-2,2-dibromo-3-nitrilopropionamide and the like; especially 2,2-dibromo-3-nitrilopropionamide.

The aqueous antimicrobial compositions of the invention normally contain from about 1 to about 25 percent by weight of the hereinbefore described halogenated amide antimicrobial based upon the total weight of the composition. However, the decomposition of the halogenated amide antimicrobials has been observed to be more pronounced when the aqueous compositions contain less than about 20 percent by weight of the antimicrobial on a total weight basis. Thus, stabilized aqueous antimicrobial compositions which, by virtue of the relatively more pronounced benefits of stabilization, are of particular interest comprise from about 1 to about 15, preferably from about 1 to about 10, most preferably from about 1 to about 5, weight percent of the total composition.

In the composition of this invention, the aforementioned halogenated amide antimicrobial is dissolved in a mixture of water and a water miscible organic solvent. Suitable organic solvents include any water miscible organic solvent in which the halogenated amide antimicrobial is at least partially soluble. Preferably the organic solvent is one in which the halogenated amide antimicrobial is soluble at normal room temperature (i.e., from about 20° to about 25° C.) to the extent of at least about 5 parts by weight of the antimicrobial in about 95 parts by weight of the solvent. The most preferred water miscible organic solvents are those in which the antimicrobial is soluble to the extent of at least about 10 (especially at least about 20) parts by weight of the antimicrobial in about 80 parts by weight of the solvent at normal room temperatures (i.e., from about 20° to about 25° C.).

Advantageously, the organic solvent is a polyalkylene glycol or an ether thereof, especially a normally liquid straight chain polyalkylene glycol or a mono- or di-saturated hydrocarbyl ether thereof wherein the term "saturated hydrocarbyl" refers to a monovalent saturated hydrocarbon radical as hereinbefore defined.

Generally, such polyalkylene glycols and polyalkylene glycol ethers have a weight average molecular weight (Mw) of from about 75 to about 1000. Such average molecular weights are hereinafter designated for the particular glycols involved by placing a numeral representing the weight average molecular weight after the glycol name.

Of particular interest in the practice of the invention are the polyalkylene glycols of the ethylene, trimethylene or tetramethylene series and the mono- and di-lower (e.g., containing from 1 to about 6 carbon atoms) saturated hydrocarbyl ethers thereof. Examples of such particularly advantageous solvents include polyethylene glycols, trimethylene glycols, tetramethylene glycols and the mono- and di-lower saturated hydrocarbyl (e.g., lower alkyl and phenyl) ethers of such glycols.

Examples of the aforementioned polyalkylene glycols and ethers include 1,4-butanediol, triethylene glycol, polyethylene glycol 200, tetraethylene glycol, polyethylene glycol 400, diethylene glycol dimethyl ether, diethylene glycol phenyl ether, diethylene glycol ethyl phenyl ether, polytrimethylene glycol 200, diethylene glycol, triethylene glycol methyl ether and polyethylene glycol 600.

Preferably, the polyalkylene glycol or ether ingredient is a polyethylene glycol, or a mixture of polyethylene glycols, having Mw of from about 175 to about 250. Most preferably the polyalkylene glycol ingredient is polyethylene glycol 200.

The amount of the aforementioned water miscible organic solvent employed in the practice of the invention is not particularly critical. Advantageously, however, a sufficient amount is employed to prevent precipitation of the halogenated amide antimicrobial during shipping, storage and use of the aqueous antimicrobial composition. The amount of the organic solvent desirably employed will thus depend upon such factors as the solubility of the halogenated amide antimicrobial in the organic solvent, the desired concentration of the halogenated amide antimicrobial in the composition, and the like. However, as a general rule the organic solvent constitutes from about 5 to about 90, preferably from about 10 to about 80, more preferably from about 25 to about 75, most preferably from about 35 to about 70, percent by weight of the total antimicrobial composition.

As has been noted, any of the aforementioned water miscible organic solvents can be suitably employed in the practice of this invention to dissolve the aforementioned halogenated amide antimicrobial. However, it has been found (and such finding constitutes the subject matter of a commonly owned application by George A. Burk, Charles A. Wilson and Charles E. Reineke, filed even date herewith) that the aforementioned problem of halogenated amide decomposition under aqueous conditions is substantially more pronounced in the presence of salts of organic acids and/or glycols having a molecular weight of less than about 70 grams per mole; both of which, for example, are potentially common minor impurities in many commercially available unpurified polyalkylene glycols and ethers thereof, Thus, the benefits attributable to the herein disclosed stabilizers are relatively more pronounced in those stabilized aqueous antimicrobial compositions which employ organic solvents containing the aforementioned impurities or which contain such impurities from some other source.

The amount of water contained by the aqueous antimicrobial composition of the invention is likewise not particularly critical to the practice of the invention. However, as a general rule the compositions of the invention employ water in an amount of from about 5 to about 90, preferably from about 10 to about 85, more preferably from about 15 to about 70, most preferably from about 20 to about 60 weight percent based upon the weight of the total antimicrobial composition.

The carbamoyl or sulfamoyl stabilizers employed in the practice of this invention are saturated (i.e., free of carbon to carbon unsaturation) aliphatic or alicyclic compounds (a) which contain a moiety of the formula $-N(R_3)C(O)-$ or a moiety of the formula $-N(R_3)S(O)_2-$ wherein $R_3$ is hydrogen or lower alkyl and (b) which are different from the halogenated amide antimicrobial employed.

Advantageously, such carbamoyl or sulfamoyl stabilizers do not contain halogen atoms (i.e., are non-halogenated). Especially advantageous carbamoyl or sulfamoyl stabilizers can be represented by the formula:

$$R_2-Q-N(R_3)_2 \qquad \text{II}$$

wherein Q is a carbonyl radical

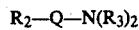

(i.e., $-\overset{\overset{\displaystyle O}{\|}}{C}-$)

or a sulfonyl radical

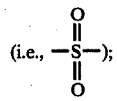

(i.e., $-\overset{\overset{\displaystyle O}{\|}}{\underset{\underset{\displaystyle O}{\|}}{S}}-$);

$R_2$ is a radical selected from the group consisting of $R_4$, $-N(R_4)_2$, $-C(O)N(R_4)_2$, and $-NHC(O)N(R_4)_2$ wherein each $R_4$ independently is hydrogen or lower alkyl; and each $R_3$ radical independently is selected from the group consisting of hydrogen, and lower alkyl; or one of the $R_3$ groups and the $R_2$ group, in combination, jointly form a divalent radical selected from the group consisting of $-(CH_2)_3-$, $-(CH_2)_4-$, $-(CH_2)_5-$, $-C(O)CH_2CH_2-$ and $-C(O)C(R_4)_2N(R_4)-$ wherein $R_4$ is as hereinbefore defined.

The carbamoyl and sulfamoyl stabilizers of the formula II thus include saturated aliphatic compounds corresponding to the formula II wherein Q is —C(O)— or —S(O)$_2$—, preferably —C(O)—; R$_2$ is —R$_3$, —N(R$_3$)$_2$, —C(O)N(R$_3$)$_2$, —NHC(O)N(R$_3$)$_2$; and each R$_3$ independently hydrogen or lower alkyl, preferably hydrogen, methyl or ethyl. Such saturated aliphatic carbamoyl or sulfamoyl compounds include, for example, urea and lower alkyl N-substituted ureas; biuret and lower alkyl N-substituted biurets; sulfamide and lower alkyl N-substituted sulfamides; oxamide and lower alkyl N-substituted oxamides; and lower alkyl N-substituted amides. In the aforementioned carbamoyl or sulfamoyl compounds the lower alkyl nitrogen substituent is preferably methyl or ethyl.

The carbamoyl or sulfamoyl stabilizers of the formula II also include saturated alicyclic compounds corresponding to the formula II wherein Q is —C(O)— or —S(O)$_2$—, preferably —C(O)—; one of the R$_3$ groups and the R$_2$ group, in combination, jointly form divalent radicals selected from the group consisting of —(CH$_2$)$_3$—, —(CH$_2$)$_4$—, —(CH$_2$)$_5$—, —C(O)CH$_2$CH$_2$— and —C(O)C(R$_4$)$_2$NR$_4$— wherein each R$_4$ independently is hydrogen or lower alkyl (preferably hydrogen, methyl or ethyl); and the remaining R$_3$ group is hydrogen or lower alkyl, preferably hydrogen, methyl or ethyl. Such saturated alicyclic carbamoyl or sulfamoyl compounds include, for example, caprolactam, valerolactam, 2-pyrrolidone, hydantoin, succinimide and the lower alkyl N-substituted counterparts thereof wherein the lower alkyl nitrogen substituent is preferably methyl or ethyl.

Examples of the saturated aliphatic or saturated alicyclic stabilizers suitably employed in the practice of this invention thus include urea, N-methyl urea, N-propyl urea, N,N-diethyl urea, N-methyl-N-butyl urea, N-propyl-N'-ethyl urea, biuret, sulfamide, N,N-dimethyl sulfamide, oxamide, N-ethyl-N'-ethyl oxamide, N,N-dimethylformamide, caprolactam, valerolactam, 2-pyrrolidone, N-methyl-2-pyrrolidone, dimethylhydantoin, succinimide and the like.

Preferred stabilizers are urea, N-methyl urea, N,N-diethyl urea, biuret, sulfamide, oxamide, N,N-dimethylformamide, caprolactam, N-methyl-2-pyrrolidone, dimethylhydantoin, and succinimide.

The most preferred stabilizers are urea, N-methyl urea, N,N-diethyl urea, biuret, caprolactam and succinimide (especially caprolactam or succinimide).

The hereinbefore described carbamoyl or sulfamoyl stabilizer is employed in the practice of the invention in a "stabilizing amount", which term is defined hereinbefore. Advantageously, such stabilizer is employed in an amount sufficient to reduce by at least about 20 percent (preferably by at least about 30 percent and most preferably by at least about 40 percent) the amount of antimicrobial compound which decomposes during about 15 days (preferably about 30 days) of storage at 50° C. Such decomposition reduction is, of course, relative to that which occurs under the same conditions in the absence of the aforementioned stabilizer. In quantitative terms, the amount of stabilizer needed to achieve the desired degree of stabilization can vary depending upon the remainder of the composition (i.e., the identity and concentration of the other ingredients in the particular composition involved) and upon the particular stabilizer employed. However, as a general rule the stabilizer constitutes between about 0.05 and about 10, preferably between about 0.1 and about 5, most preferably between about 0.5 and about 2, percent by weight of the total composition.

In addition to the hereinbefore defined ingredients, the aqueous antimicrobial composition of the invention can optionally contain other ingredients. Such optional ingredients can be inert in the sense that they neither inhibit nor accelerate decomposition of the antimicrobial compound. Alternatively, such optional ingredients can themselves be stabilizers for the halogenated amide antimicrobial. Thus, for example, the stabilized aqueous antimicrobial composition of the invention can, in addition to the aforementioned carbamoyl or sulfamoyl stabilizer, further comprise other compounds which are stabilizers in their own right as disclosed in commonly owned applications filed even date herewith. Suitable optional additional stabilizers thus include acids or anhydrides (e.g., acetic acid, ethylenediaminetetraacetic acid, succinic acid, succinic anhydride, glycolic acid, etc.) as disclosed by George A. Burk; cyclic ethers (e.g., 1,4-dioxane, tetrahydrofuran, sym-trioxane, N-methyl morpholine, etc.) as disclosed by George A. Burk and Charles A. Wilson; aldehydes (e.g., formaldehyde, paraformaldehyde, vanillin, etc.) as disclosed by George A. Burk, Charles A. Wilson and Charles E. Reineke; quaternary salts (e.g., methyl triphenyl phosphonium bromide, n—C$_{12}$—C$_{18}$ alkyl dimethyl benzyl ammonium chloride, etc.) as disclosed by George A. Burk; and azine or nitrile compounds (e.g., cyanuric acid, 2-chloro-4,6-bis(ethylamino)-s-triazine, cyanoguanidine, succinonitrile, etc.) as disclosed by George A. Burk. The amount of such additional stabilizer which is optionally employed varies depending upon a number of factors, such as the identity and amounts of the specific ingredients involved. However, when such additional stabilizer is employed, it is generally used in an amount between about 0.1 and about 2 (preferably between about 0.2 and about 1) percent by weight based upon the total weight of the antimicrobial composition.

The order of combination of the hereinbefore described ingredients is not critical to the obtention of a decreased decomposition rate relative to that obtained with the corresponding non-stabilized composition. However, in order to avoid excessive amounts of decomposition prior to stabilization, it is generally desirable to avoid prolonged exposure of the antimicrobial compound to the water in the composition prior to addition of the stabilizer thereto. In addition, it is generally desirable, in order to retain optimum antimicrobial activity, to prepare, store, transport and handle the stabilized compositions of the invention at the lowest practicable temperature (normally ambient temperature). Similarly, it is desirable that the pH of the composition be maintained at a value between about 2 and about 5 (preferably between about 3 and about 4) since the decomposition of the antimicrobial under aqueous conditions (both with and without stabilization) is typically minimized within such pH range.

As has been noted, the hereinbefore described stabilizers have been found to reduce the halogenated amide antimicrobial decomposition rate in a mixture of an organic solvent and water. A particularly beneficial result of such phenomenon is that suitably stable halogenated amide antimicrobial compositions can be prepared directly from a mixture of the antimicrobial and the aqueous reaction medium in which it was prepared. Specifically, separation of the halogenated amide antimicrobial from its aqueous reaction medium is conveniently eliminated by incorporating such reaction medium into the antimicrobial composition and by counteracting the adverse impact of the water thereby introduced into such composition by adding the aforementioned carbamoyl or sulfamoyl stabilizer.

Thus, in one aspect this invention is a process for preparing the aforementioned stabilized aqueous antimicrobial compositions, which process comprises the steps of (a) preparing the halogenated amide antimicrobial by the acid catalyzed reaction of the corresponding non-halogenated amide with halogen in aqueous solution; (b) dissolving the resulting aqueous reaction mixture in the hereinbefore described water miscible organic solvent; and (c) adding to the reaction mixture, or to the water soluble organic solvent solution thereof, a stabilizing amount of the aforementioned carbamoyl stabilizer which is different from the halogenated amide antimicrobial and from the corresponding non-halogenated amide, the aforementioned sulfamoyl stabilizer or a combination thereof. Typically, the aforementioned process also comprises an additional step in which the pH of the reaction mixture, the organic solvent solution, or the stabilized organic solvent solution is adjusted such that the pH of the antimicrobial composition is from about 3 to about 5, preferably from about 3 to about 4. Preferably, such pH adjustment step is performed following preparation of the halogenated amide and prior to dissolution of the reaction mixture in the organic solvent. In such instance, adjustment of the pH to a value of from about 5 to about 7 (preferably from about 5.5 to about 6.5) prior to dissolution typically provides the antimicrobial composition with a pH within the desired range following the dissolution step.

The particular reagent employed in the aforementioned pH adjustment step is not particularly critical. However, as a general rule, alkali metal or alkaline earth metal carbonates or bicarbonates (especially sodium carbonate) are advantageously employed.

The preparation of the halogenated amide antimicrobial (i.e., step (a) above) can be accomplished in any convenient conventional manner. Thus, for example, the halogenated amide antimicrobial can be prepared by the acid catalyzed reaction of the corresponding non-halogenated amide (e.g., cyanoacetamide, malonic diamide, and N-substituted derivatives thereof) with halogen (especially bromine) in aqueous solution, preferably at a temperature of less than about 40° C. and preferably at a hydrogen halide (which is a reaction by-product) concentration of less than about 20 weight percent on a total weight basis.

Preferably, however, the initial step of such process is performed pursuant to the improved procedure which is disclosed by U.S. Pat. No. 3,751,444. In such preferred process for preparing the halogenated amide antimicrobial, the improved aspect comprises introducing a water-soluble bromate into the aqueous reaction medium. Further details relating to the practice of such preferred initial step are found in U.S. Pat. No. 3,751,444, the disclosure of which is hereby incorporated by reference.

After the halogenated amide antimicrobial has been prepared in the aforementioned manner, the resulting reaction mixture is dissolved in the hereinbefore described organic solvent. Such dissolution step is performed either before or after addition of the stabilizer and without isolation of the halogenated amide antimicrobial from the aqueous reaction medium. Any of the hereinbefore described water miscible organic solvents can be suitably employed in such dissolution step. However, as has been noted, the presence in such solvent of salts of organic acids and/or glycols having a molecular weight of less than about 70 has been observed to deleteriously affect the stability of the halogenated amide antimicrobial. Accordingly, it is preferable (in order to obtain optimum stability in the resulting compositions of the instant process) to employ an organic solvent of the hereinbefore described type which is substantially free both of salts of organic acids and of glycols having molecular weights of less than about 70 grams per mole.

In the aforementioned process, it is generally desirable to avoid prolonged exposure of the halogenated amide antimicrobial to the aqueous reaction medium in the absence of the stabilizer in order to prevent excessive loss (i.e., decomposition) of the halogenated amide product prior to stabilization. In addition, the pH adjustment step is also desirably accomplished without prolonged delay since the decomposition rate of the halogenated amide antimicrobial is generally pH dependent and since such decomposition rate is typically minimized within the indicated pH range. In addition, since the rate of decomposition of the halogenated amide antimicrobial increases with increased temperature, it is preferable to conduct the aforementioned individual process steps (and to store, transport and handle the resulting aqueous antimicrobial compositions) at ambient temperature (e.g., from about 20° to about 25° C.) or less in order to avoid excessive decomposition of the antimicrobial during such operations.

Naturally, in the practice of the aforementioned process, other ingredients such as those decribed hereinbefore, can be added to the aqueous composition either during or after its preparation pursuant to such process.

The practice of the instant invention is further illustrated by the following examples. In such examples all weight percentages are on a total weight basis unless otherwise indicated. The polyethylene glycol employed in such examples is a commercial grade mixture of polyethylene glycols having a weight average molecular weight of about 200 and commercially available as Polyglycol E-200 from The Dow Chemical Company.

EXAMPLES 1 and 2

Sulfamide Stabilization of a Composition Comprising 2,2-dibromo-3-nitrilopropionamide, Polyethylene Glycol 200 and Water These experiments illustrate the increased rate of DBNPA decomposition in the presence of water. The stabilizing effect of sulfamide and of a sulfamide/acetic acid mixture upon aqueous compositions is also illustrated.

EXAMPLE 1

A 2.5 g portion of 2,2-dibromo-3-nitrilopropionamide (DBNPA) is placed in a 2 oz. amber bottle. To this is added 23.5 g of polyethylene glycol 200 (P.E.G. 200), 23.5 g of water and 0.5 g of sulfamide (i.e., $SO_2(NH_2)_2$).

EXAMPLE 2

In a second 2 oz. amber bottle is placed 2.5 g of DBNPA, 23.5 g of P.E.G. 200, 23.5 g of water, 0.25 g of sulfamide and 0.25 g of acetic acid.

CONTROL 1

In a third 2 oz. amber bottle is placed 2.5 g of DBNPA and 47.5 g of P.E.G. 200.

CONTROL 2

In a fourth 2 oz. amber bottle is placed 2.5 g of DBNPA, 23.75 g of P.E.G. 200 and 23.75 g of water.

The contents of each of the four bottles are mixed until all of the ingredients are dissolved. The dissolution is accompanied by a temperature rise of about 5° C. After the heat of dissolution has dissipated, the initial DBNPA content is verified by iodometry. The bottles are then closed with a polyethylene lined cap and placed in a constant temperature oven at 50° C. for accelerated decomposition testing. The samples are removed periodically and the extent of DBNPA decomposition is determined by iodometry. The results of the accelerated decomposition testing are presented in Table I below.

In these examples (and in the subsequent examples), the relative DBNPA content of the various antimicrobial compositions is determined by iodometry. In such test method, an excess of potassium iodide (KI) is added to the antimicrobial composition and the amount of elemental iodine which has been liberated from the KI (via oxidation of the KI by the DBNPA) is determined by titration with a standard solution of sodium thiosulfate. The amount of DBNPA present in the composition tested is then calculated on the basis of the amount of elemental iodine liberated thereby.

It should be noted that since certain of the intermediate decomposition products of DBNPA are also oxidizing agents, the indicated test method does not, strictly speaking, provide an exact measure of DBNPA content. However, such test method does provide a measure of the amount of DBNPA which has completely decomposed to the ultimate non-oxidizing species and thus provides a relative measure of the stability of the DBNPA compositions tested.

TABLE I

DBNPA CONTENTS AFTER VARIOUS STORAGE PERIODS AT 50° C.

| Example Number | Composition[1] P.E.G. 200 | Water | Stabilizer Type | Amount | Initial DBNPA Content | DBNPA Content After the Indicated Storage Period at 50° C.[1] 5 Days | 13 Days | 21 Days | 26 Days |
|---|---|---|---|---|---|---|---|---|---|
| 1 | 47% | 47% | Sulfamide | 1% | 5.10% | 5.02% | 4.85% | 4.57% | 4.25% |
| 2 | 47% | 47% | Sulfamide/ Acetic Acid | 0.5% 0.5% | 5.20% | 5.10% | 4.92% | 4.63% | — |
| Control 1* | 95% | None | None | None | 5.0% | 4.92% | 4.80% | 4.70% | 4.50% |
| Control 2* | 47.5% | 47.5% | None | None | 5.0% | 4.68% | 4.18% | 3.72% | 3.45% |

*Not an example of the invention.
[1]The indicated percentages are in weight percent on a total weight basis.

Comparison of controls 1 and 2 illustrates the adverse effect of water upon the stability of DBNPA. For example, under aqueous conditions (i.e., Control 2) 31 percent of the DBNPA which was originally present decomposes during 26 days at 50° C., i.e., [(5.0−3.45)÷5.0]×100%. In contrast, the composition of Control 1 (i.e., containing substantially no water) suffers a loss of only 10 percent of the DBNPA originally present) over the same time period at 50° C., i.e., [(5.0−4.5)÷5.0]×100%. Similar differences in DBNPA decomposition between Control 2 and Control 1 are reflected at the shorter test intervals.

The stabilizing effect of the sulfamide and the sulfamide-acetic acid mixture in the aqueous composition is observed by comparing Examples 1 and 2, respectively, with Control 2. Such comparison shows that the compositions of the invention, i.e., Examples 1 and 2, each exhibit substantially less DBNPA decomposition after each storage interval than does the composition of Control 2 after that same storage interval. In particular, it is also noted that, in Example 1, the sulfamide stabilizer prevented about 46 percent of the DBNPA decomposition which occurs in its absence (i.e., in Control 2) during 26 days at 50° C. In addition, it is noted that, in Example 2, the sulfamide-acetic acid mixture prevented about 57 percent of the DBNPA decomposition which occurs in its absence (i.e., in Control 2) during 21 days at 50° C.

EXAMPLE 3

Aqueous Solution of DBNPA in P.E.G. 200 Stabilized with Urea

Pursuant to the procedure of Examples 1 and 2 a solution containing 5 percent by weight DBNPA, 47 percent by weight P.E.G. 200, 47 percent by weight water, and 1 percent by weight urea is prepared, thereby forming the composition of Example 3. In addition a solution (Control 3A) containing 5 weight percent DBNPA and 95 weight percent P.E.G. 200 and a solution (Control 3B) containing 5 weight percent DBNPA and 95 weight percent of a 50:50 (by weight) mixture of water and P.E.G. 200 are prepared for comparison.

The three solutions are stored at 50° C. for accelerated decomposition testing, with samples being removed periodically for determination of DBNPA content by iodometry. The test results are presented below.

| | DBNPA CONCENTRATION (IN WEIGHT PERCENT ON A TOTAL WEIGHT BASIS) AFTER THE INDICATED STORAGE TIME AT 50° C. | | | |
|---|---|---|---|---|
| | Initial DBNPA Content | 7 Days | 15 Days | 33 Days |
| Example 3 | 5.02 | 4.82 | 4.47 | 3.88 |
| Control 3A* | 5.00 | 4.89 | 4.76 | 4.38 |
| Control 3B* | 5.00 | 4.55 | 4.02 | 3.30 |

*Not an example of the invention.

The adverse effect of water upon the stability of DBNPA is again observed by comparing Control 3B with Control 3A. The stabilizing effect of urea is observed by comparing the DBNPA content of Example 3 with that of Control 3B at the various storage intervals.

EXAMPLE 4

Aqueous Solution of DBNPA in P.E.G. 200 Stabilized with a 1:1 Urea-Acetic Acid Mixture The composition of Example 4 is prepared by forming a solution containing 5 weight percent DBNPA, 47 weight percent P.E.G. 200, 47 weight percent water, 0.5 weight percent urea and 0.5 weight percent acetic acid. The composition is stored at 50° C., sampled and analyzed pursuant to the procedure of Examples 1 and 2. Similarly, nonstabilized, anhydrous and aqueous compositions (i.e., Controls 4A and 4B respectively) corresponding in composition to Controls 1 and 2 of Examples 1 and 2 are prepared, aged, sampled and analyzed for comparison. The test results are presented below. In addition, the amount of DBNPA decomposition after 29 days in terms of the percent of the DBNPA which was initially present that has decomposed is also shown.

|  | DBNPA CONCENTRATION AFTER THE INDICATED STORAGE TIME AT 50° C. | | | | PERCENT OF THE INITIAL DBNPA WHICH DECOMPOSED |
|---|---|---|---|---|---|
|  | Initial | 7 Days | 15 Days | 20 Days | 29 Days | OVER 29 Days |
| Example 4 | 5.0 | 5.0 | 4.67 | 4.40 | 3.85 | 23% |
| Control 4A* | 5.0 | 4.89 | 4.76 | 4.70 | 4.40 | 12% |
| Control 4B* | 5.0 | 4.55 | 4.02 | 3.70 | 3.40 | 32% |

*Not an example of the invention

The results again show that under aqueous conditions (i.e., Control 4B) the DBNPA decomposition is substantially greater than under anhydrous conditions (i.e., Control 4A). The results also show that the extent of such decomposition under aqueous conditions is substantially reduced by the presence of the urea and acetic acid. Specifically, the composition of Example 3 exhibits 28 percent $$\text{(i.e., } \frac{32 - 23}{32} \times 100\%\text{)}$$

less decomposition after 29 days than does the nonstabilized composition of Control 4B.

EXAMPLE 5

Aqueous Solution of DBNPA in P.E.G. 200 Stabilized with Oxamide

The composition of Example 5 is prepared by forming a solution containing 5 weight percent DBNPA, 47 weight percent P.E.G. 200, 47 weight percent water and 1 weight percent oxamide. Such composition is stored at 50° C., sampled and analyzed pursuant to the procedure of Examples 1 and 2. Similarly, nonstabilized compositions (Controls 5A and 5B) corresponding in compositions to those of Controls 1 and 2, respectively, of Examples 1 and 2 are prepared, aged, sampled and analyzed for comparison. The test results are presented below. In addition, the percentage of the initial DBNPA which has decomposed after 22 days is also shown.

|  | DBNPA CONCENTRATION AFTER THE INDICATED STORAGE TIME AT 50° C. | | | PERCENTAGE OF INITIAL DBNPA LOST AFTER |
|---|---|---|---|---|
|  | Initial | 13 Days | 22 Days | 22 DAYS |
| Example 5 | 5.0 | 4.20 | 4.16 | 16.8% |
| Control 5A* | 5.0 | 4.78 | 4.68 | 6.4% |
| Control 5B* | 5.0 | 4.05 | 3.70 | 26% |

*Not an example of the invention.

The results again indicate that the water of Control 5B accentuates the decomposition of DBNPA which otherwise occurs (i.e., in Control 5A). In addition, the presence of the oxamide is seen to reduce the extent of such decomposition. (Compare Example 5 with Control 5B.) In particular, it is seen that the oxamide reduces the amount of DBNPA decomposition which occurs over 22 days by about 35 percent $$\text{(i.e., } \frac{26 - 16.8}{26} \times 100\%\text{)}$$

based upon the amount occurring in its absence (i.e., in Control 5B).

EXAMPLE 6

Aqueous Solution of DBNPA in P.E.G. 200 Stabilized with Succinimide

The composition of Example 6 is prepared by forming a solution containing 5 weight percent DBNPA, 47 weight percent P.E.G. 200, 47 weight percent water and 1 weight percent succinimide. Such composition is stored at 50° C., sampled, and analyzed pursuant to the procedure of Examples 1 and 2.

After 11 days at 50° C., the composition of Example 6 is found to contain 4.81 weight percent DBNPA on a total weight basis. This represents decomposition of 3.8 percent of the DBNPA which was originally present.

After 28 days at 50° C. the composition of Example 6 is found to contain 4.43 weight percent DBNPA on a total weight basis. This represents decomposition of 11.4 percent of the DBNPA which was originally present.

In comparison, 31 percent of the initial DBNPA is observed to decompose after only 26 days at 50° C. in a corresponding aqueous composition having no stabilizer. See Control 2 in Table II above. Accordingly, the succinimide is found to prevent at least about 63 percent $$\text{(i.e., } \frac{31 - 11.4}{31} \times 100\%\text{)}$$

of the DBNPA decomposition which occurs in its absence over a 28-day period at 50° C.

EXAMPLES 7-13

Stabilized Formulations of DBNPA in Aqueous P.E.G. 200

Solutions containing 5 weight percent DBNPA, 47 weight percent P.E.G. 200, 47 weight percent water and 1 weight percent of the indicated stabilizer are prepared, aged at 50° C., sampled and analyzed pursuant to the procedure of Examples 1 and 2. The retained DBNPA contents are presented below. For comparison, there is also presented data from Control 3B which has the same (i.e., 15 days) or shorter (i.e., 33 days) sampling intervals.

TABLE II

DBNPA CONCENTRATION AND PERCENT OF INITIAL DBNPA DECOMPOSED AS A FUNCTION OF TIME AT 50° C.

| | | DBNPA Concentration[1] After the Indicated Storage Time at 50° C. | | | | Percentage of Initial DBNPA Decomposed[2] | | |
|---|---|---|---|---|---|---|---|---|
| | Stabilizer | 15 Days | 25 Days | 33 Days | 35 Days | 15 Days | 33 Days | 35 Days |
| Control 3B* | None | 4.02 | — | 3.30 | — | 19.6% | 34% | |
| Example 7 | Methyl Urea | 4.7 | 4.4 | | 4.1 | 6% | | 18% |
| Example 8 | Diethyl Urea | 4.65 | 4.4 | | 4.1 | 7% | | 18% |
| Example 9 | Biuret | 4.7 | 4.5 | | 4.1 | 6% | | 18% |
| Example 10 | N,N-Dimethyl Formamide | 4.7 | 4.3 | | 3.7 | 6% | | 26% |
| Example 11 | Caprolactam | 4.75 | 4.55 | | 4.35 | 5% | | 13% |
| Example 12 | Methyl Pyrrolidone | 4.85 | 4.2 | | N/A | 3% | | — |
| Example 13 | Dimethyl Hydantoin | 4.7 | 4.4 | | N/A | 6% | | — |

*Not an example of the invention.
[1]In weight percent on a total weight basis.
[2]Calculated as follows:
$$\frac{\text{Initial DBNPA Content (i.e., 5 wt \%)} - \text{DBNPA Content After Specified Interval}}{\text{Initial DBNPA Content}} \times 100\%$$

From the results of Table II (in the form of the percentage of the initial DBNPA which has decomposed), the effectiveness of the stabilizers is calculated in terms of the percentage of the DBNPA decomposition which is prevented by the individual stabilizers. The results are as follows:

| | | Percent of the DBNPA Decomposition Which is Prevented | |
|---|---|---|---|
| Example | Stabilizer | 15 Days | 35 Days |
| 7 | Methyl Urea | 69% | 47% |
| 8 | Diethyl Urea | 64% | 47% |
| 9 | Biuret | 69% | 47% |
| 10 | N,N-Dimethyl Formamide | 69% | 24% |
| 11 | Caprolactam | 74% | 62% |
| 12 | Methyl Pyrrolidone | 85% | — |
| 13 | Dimethyl Hydantoin | 69% | — |

[1]Calculated as follows:*
$$\frac{\% \text{ Decomposed for Control 3B at 33 Days (i.e., 34)} - \% \text{ Decomposed for Example @ 35 Days}}{\% \text{ Decomposed for Control 3B at 33 Days (i.e., 34)}} \times 100\%$$
*Note that the 35-day decomposition prevention figure is conservative (i.e., smaller than the actual value) since the percent decomposition at 35 days for Control 3B would be larger than the 33-day figure which is employed in the calculation.

As is apparent from the foregoing results, each of the various stabilized aqueous compositions exhibit higher DBNPA contents after the various periods of storage at 50° C. than does Control 3B after the same or shorter 50° C. storage periods. In addition, the results show that each of the stabilizers prevents more than 20 percent of the DBNPA decomposition which occurs in the absence of such stabilizers over a 35-day storage period at 50° C.

Pursuant to the foregoing procedure, other compounds (i.e., acetamide, uracil, parabamic acid, barbituric acid, 2,3-dichloromaleamide, 2-cyanoacetamide, 1,3-dibromo-5,5-dimethylhydantoin, trichloroisocyanurate and thiourea) are tested as possible stabilizers in compositions containing 5 weight percent DBNPA, 47 weight percent P.E.G. 200, 47 weight percent water and 1 weight percent of the possible stabilizer compound. In the indicated compositions, none of such compounds provide significant stabilization after 30 days at 50° C. In fact, many of such compounds are observed to have a substantial destabilizing effect.

While the practice of the invention has been illustrated with reference to particular embodiments and examples, it should be understood that such embodiments and examples are not intended to limit the scope of the instantly claimed invention.

What is claimed is:

1. An aqueous antimicrobial composition having a pH of from about 2 to about 5 and comprising:

(a) an alpha-halogenated amide antimicrobial compound of the formula:

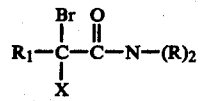

wherein:
X is hydrogen, halogen or a cyano radical;
each R group is independently hydrogen, a monovalent saturated hydrocarbon radical or an inertly substituted monovalent saturated hydrocarbon radical or the two R groups are jointly a divalent saturated hydrocarbon radical or an inertly substituted divalent saturated hydrocarbon radical which, taken with the adjacent nitrogen atom, forms a heterocyclic ring having from 4 to about 10 ring members; and $R_1$ is a cyano radical or an amido radical of the formula:

wherein R is as hereinbefore defined;
(b) a water-miscible organic solvent in an amount sufficient to dissolve the halogenated amide antimicrobial, said solvent being a normally liquid straight chain polyalkylene glycol of the ethylene, trimethylene or tetramethylene series or a mono- or di-saturated hydrocarbyl ether thereof;
(c) water; and
(d) a stabilizing amount of a carbamoyl or sulfamoyl stabilizer wherein said stabilizing amount is an amount of the carbamoyl or sulfamoyl stabilizer which is sufficient to measurably reduce the decomposition rate of the halogenated amide in the aqueous antimicrobial composition and wherein said carbamoyl or sulfamoyl stabilizer corresponds to the formula:

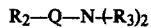

in which:
Q is a carbonyl radical or a sulfonyl radical;
$R_2$ is a radical selected from the group consisting of: $R_4$, $-N(R_4)_2$, $-C(O)N(R_4)_2$, and $-NH\ C(O)N(R_4)_2$ wherein each $R_4$ independently is hydrogen or lower alkyl; and
each $R_3$ radical is independently selected from the group consisting of hydrogen and lower alkyl; or
one of the $R_3$ groups and the $R_2$ group, in combination, jointly form a divalent radical selected from the group consisting of $-(CH_2)_3-$, $-(CH_2)_4-$, $-(CH_2)_5-$, $-C(O)CH_2CH_2-$ and $-C(O)C(R_4)_2N(R_4)-$ wherein $R_4$ is as hereinbefore defined.

2. The composition of claim 1 wherein the polyalkylene glycol or ether thereof has a weight average molecular weight of from about 75 to about 1000.

3. The composition of claim 1 wherein, in the antimicrobial compound:
X is hydrogen, chlorine or bromine;
each R group is independently hydrogen, a monovalent saturated hydrocarbon radical or an inertly substituted monovalent saturated hydrocarbon radical; and
$R_1$ is a cyano radical.

4. The composition of claim 1 wherein, in the antimicrobial compound:
X is hydrogen, chlorine or bromine and $R_1$ is a cyano radical.

5. The composition of claim 1 wherein the antimicrobial compound is 2,2-dibromo-3-nitrilopropionamide.

6. The composition of claim 1 wherein the carbamoyl or sulfamoyl stabilizer is selected from the group consisting of urea, N-methyl urea, N-propyl urea, N,N-diethyl urea, N-methyl-N-butyl urea, N-propyl-N'-ethyl urea, biuret, sulfamide, N,N-dimethyl sulfamide, oxamide, N-ethyl-N'-ethyl oxamide, N,N-dimethylformamide, caprolactam, valerolactam, 2-pyrrolidone, N-methyl-2-pyrrolidone, dimethylhydantoin and succinimide.

7. The composition of claim 1 wherein the carbamoyl or sulfamoyl stabilizer is selected from the group consisting of urea, N-methyl urea, N,N-diethyl urea, biuret, sulfamide, oxamide, N,N-dimethylformamide, caprolactam, N-methyl-2-pyrrolidone, dimethylhydantoin and succinimide.

8. The composition of claim 7 wherein the water-soluble organic solvent is polyethylene glycol, having a weight average molecular weight of about 200; the antimicrobial compound is 2,2-dibromo-3-nitrilopropionamide; and the pH of the aqueous antimicrobial composition is from about 3 to about 4.

9. The composition of claim 1 wherein the carbamoyl or sulfamoyl stabilizer is caprolactam or succinimide.

10. The composition of claim 1 wherein:
(a) the antimicrobial compound constitutes from about 1 to about 25 weight percent of the total composition;
(b) the water constitutes from about 20 to about 60 weight percent of the total composition;
(c) the water miscible organic solvent constitutes from about 25 to about 75 weight percent of the total composition; and
(d) the carbamoyl or sulfamoyl stabilizer constitutes from about 0.1 to about 5 weight percent of the total composition.

11. A process for preparing the aqueous antimicrobial composition of claim 1 which process comprises the steps of:
(a) preparing the alpha-halogenated amide antimicrobial by the acid catalyzed reaction of the corresponding nonhalogenated amide with halogen in aqueous solution, at a temperature of less than about 40° C. and at a hydrogen halide concentration which is less than about 20 weight percent on a total weight basis but which is sufficient to catalyze the reaction;
(b) dissolving the resulting aqueous reaction mixture in the water miscible organic solvent;
(c) adding to the reaction mixture of step (a), or to the water miscible organic solvent solution of step (b), a stabilizing amount of the carbamoyl or sulfamoyl stabilizer; and
(d) adjusting the pH of the product of steps (a), (b) or (c) such that the aqueous antimicrobial composition has a pH of from about 2 to about 5.

12. The process of claim 11 in which the pH adjustment is such that the aqueous antimicrobial composition has a pH of from about 3 to about 4.

13. The process of claim 11 wherein the halogenated amide antimicrobial is 2,2-dibromo-3-nitrilopropionamide and the halogen is bromine; the water-miscible organic solvent is polyethylene glycol, or a lower alkyl ether thereof, having a weight average molecular weight of about 200; and the carbamoyl or sulfamoyl stabilizer is selected from the group consisting of urea, N-methyl urea, N,N-diethyl urea, biuret, sulfamide, oxamide, N,N-dimethylformamide, caprolactam, N-methyl-2-pyrrolidone, dimethylhydantoin and succinimide.

14. The process of claim 11 wherein a water-soluble bromate is introduced to the aqueous reaction medium during preparation of the halogenated amide antimicrobial; and the pH of the aqueous reaction mixture is adjusted to a value of from about 5 to about 7 by the addition of an alkali metal, or an alkaline earth metal, carbonate or bicarbonate to such reaction mixture following preparation of the halogenated amide and prior to the dissolution of such reaction mixture in the organic solvent.

15. An aqueous antimicrobial composition having a pH of from about 2 to about 5 and comprising, based upon the total weight of such composition:
(a) from about 1 to about 25 weight percent of a halogenated amide antimicrobial of the formula:

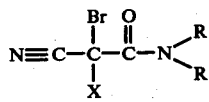

wherein X is hydrogen, chlorine or bromine and each R is independently hydrogen, an alkyl group of from 1 to about 6 carbon atoms or phenyl;
(b) from about 5 to about 90 weight percent of water;
(c) from about 5 to about 90 weight percent of a water-miscible organic solvent which is selected from the group consisting of polyethylene glycols, trimethylene glycols, tetramethylene glycols and the mono- and di- phenyl or $C_1$ to about $C_6$ alkyl ethers thereof and which has a weight average molecular weight of from about 75 to about 1000; and
(d) a stabilizing amount, in the range of from about 0.05 to about 10 weight percent, of a carbamoyl or sulfamoyl stabilizer of the formula:

wherein:
Q is a carbonyl radical or a sulfonyl radical;
$R_2$ is a radical selected from the group consisting of: $R_4$, $-N(R_4)_2$, $-C(O)N(R_4)_2$, and $-NH$ $C(O)N(R_4)_2$ wherein each $R_4$ independently is hydrogen or lower alkyl; and each $R_3$ radical is independently selected from the group consisting of hydrogen and lower alkyl; or
one of the $R_3$ groups and the $R_2$ group, in combination, jointly form a divalent radical selected from the group consisting of: $-(CH_2)_3-$, $-(CH_2)_4-$, $-(CH_2)_5-$, $-C(O)CH_2CH_2-$ and $-C(O)C(R_4)_2N(R_4)-$ wherein $R_4$ is as hereinbefore defined.

16. The composition of claim 15 wherein the halogenated amide antimicrobial is 2,2-dibromo-3-nitrilopropionamide.
17. The composition of claim 16 wherein the water-miscible organic solvent is polyethylene glycol having a weight average molecular weight of from about 175 to about 250.
18. The composition of claim 16 wherein the water-miscible organic solvent is polyethylene glycol 200.
19. The composition of claim 17 wherein the carbamoyl or sulfamoyl stabilizer is selected from the group consisting of urea, N-methyl urea, N-propyl urea, N,N-diethyl urea, N-methyl-N-butyl urea, N-propyl-N'-ethyl urea, biuret, sulfamide, N,N-dimethyl sulfamide, oxamide, N-ethyl-N'-ethyl oxamide, N,N-dimethylformamide, caprolactam, valerolactam, 2-pyrrolidone, N-methyl-2-pyrrolidone, dimethylhydrantoin and succinimide.
20. A process for preparing the aqueous antimicrobial composition of claim 19 which process comprises the steps of:
(a) preparing the 2,2-dibromo-3-nitrilopropionamide by the reaction of cyanoacetamide with bromine in aqueous solution (1) at a temperature of less than about 40° C., (2) in the presence of HBr at a concentration which is less than about 20 weight percent on a total weight basis but which is sufficient to catalyze the reaction and (3) in the presence of an alkali metal or an alkaline earth metal bromate;
(b) dissolving the resulting aqueous reaction mixture in the polyethylene glycol having a weight average molecular weight of from about 175 to about 250;
(c) adding to the reaction mixture of step (a) or to the solution thereof of step (b) a stabilizing amount of a carbamoyl or sulfamoyl stabilizer selected from the group consisting of urea, N-methyl urea, N,N-diethyl urea, biuret, sulfamide, oxamide, N,N-dimethylformamide, caprolactam, N-methyl-2-pyrrolidone, dimethylhydantoin and succinimide; and
(d) adjusting the pH of the product of step (a), (b) or (c) such that the aqueous antimicrobial composition has a pH of from about 2 to about 5.

* * * * *

UNITED STATES PATENT AND TRADEMARK OFFICE
CERTIFICATE OF CORRECTION

PATENT NO. : 4,163,797
DATED : August 7, 1979
INVENTOR(S) : George A. Burk; Charles E. Reineke It is certified that error appears in the above-identified patent and that said Letters Patent are hereby corrected as shown below:

Column 6, line 15, delete "thereof," and insert --thereof.--.

Column 9, line 24, delete "3" and insert --2--.

Column 10, line 32, delete "decribed" and insert --described--.

Column 15, line 42, fourth heading, delete "35 Days" and insert --35 Days$^1$--.

Column 20, line 17, delete "dimethylhydrantoin" and insert --dimethylhydantoin--.

Signed and Sealed this

*Thirteenth* Day of *November 1979*

[SEAL]

*Attest:*

RUTH C. MASON
*Attesting Officer*

LUTRELLE F. PARKER
*Acting Commissioner of Patents and Trademarks*